United States Patent
Feng

(10) Patent No.: US 11,957,834 B2
(45) Date of Patent: Apr. 16, 2024

(54) HEATING INHALER AND CONTROLLING METHOD THEREOF

(71) Applicant: SHENZHEN SMOORE TECHNOLOGY LIMITED, Guangdong (CN)

(72) Inventor: Qiaofang Feng, Guangdong (CN)

(73) Assignee: SHENZHEN SMOORE TECHNOLOGY LIMITED, Guangdong (CN)

( * ) Notice: Subject to any disclaimer, the term of this patent is extended or adjusted under 35 U.S.C. 154(b) by 1335 days.

(21) Appl. No.: 16/448,840

(22) Filed: Jun. 21, 2019

(65) Prior Publication Data
US 2020/0009336 A1    Jan. 9, 2020

(30) Foreign Application Priority Data

Jul. 4, 2018    (CN) .......................... 201810723694.X

(51) Int. Cl.
*A61M 15/06*    (2006.01)
*A24F 40/46*    (2020.01)
(Continued)

(52) U.S. Cl.
CPC ............. *A61M 15/06* (2013.01); *A24F 40/46* (2020.01); *A24F 40/50* (2020.01); *A24F 40/57* (2020.01);
(Continued)

(58) Field of Classification Search
CPC .......... A24F 40/57; A24F 40/53; A24F 40/51; A24F 40/50
See application file for complete search history.

(56) References Cited

U.S. PATENT DOCUMENTS

2011/0126848 A1    6/2011  Zuber et al.
2011/0155153 A1    6/2011  Thorens et al.
(Continued)

FOREIGN PATENT DOCUMENTS

| CA | 2 925 647 | 5/2015 |
|----|-----------|--------|
| CA | 2943996 A1 | 9/2015 |

(Continued)

OTHER PUBLICATIONS

Chinese Office Action dated Mar. 11, 2019 corresponding to counterpart patent application 201110457376.9.
(Continued)

*Primary Examiner* — Alex B Efta
(74) *Attorney, Agent, or Firm* — Ladas & Parry LLP

(57) ABSTRACT

The present disclosure relates to a heating inhaler and a controlling method thereof. The method includes: the sensing element detecting a suction action, and if the sensing element detects the suction action within a first predetermined time period, the control circuit board controlling the power source to supply power to the atomizer for a second predetermined time period then stop supplying, wherein the indicating element displays a first state within the second predetermined time period until the power source stops supplying power to the atomizer, then the indicating element displays a second state. If the sensing element detects no suction action within the first predetermined time period, the control circuit board controlling the power source to stop supplying the electric power to the atomizer, and the indicating element displaying the second state.

6 Claims, 7 Drawing Sheets

(51) Int. Cl.
  *A24F 40/50* (2020.01)
  *A24F 40/57* (2020.01)
  *A61M 11/04* (2006.01)
  *A61M 16/00* (2006.01)

(52) U.S. Cl.
  CPC ... *A61M 11/042* (2014.02); *A61M 2016/0024* (2013.01)

(56) References Cited

U.S. PATENT DOCUMENTS

| | | | | |
|---|---|---|---|---|
| 2013/0284192 | A1* | 10/2013 | Peleg | A24F 40/53 131/329 |
| 2014/0014125 | A1* | 1/2014 | Fernando | A24F 40/50 131/328 |
| 2014/0334804 | A1* | 11/2014 | Choi | A24F 40/485 392/404 |
| 2014/0338685 | A1* | 11/2014 | Amir | H05B 1/0244 131/329 |
| 2015/0128976 | A1* | 5/2015 | Verleur | H02J 7/0042 131/329 |

FOREIGN PATENT DOCUMENTS

| | | | |
|---|---|---|---|
| CN | H11178562 | A | 7/1999 |
| CN | 201127293 | Y | 10/2008 |
| CN | 102264420 | A | 11/2011 |
| CN | 102883766 | A | 1/2013 |
| CN | 204032371 | U | 12/2014 |
| CN | 204317489 | U | 5/2015 |
| CN | 104770877 | A | 7/2015 |
| CN | 104770895 | A | 7/2015 |
| CN | 105077598 | A | 11/2015 |
| CN | 105707981 | A | 6/2016 |
| CN | 105982360 | A | 10/2016 |
| CN | 106488714 | A | 3/2017 |
| CN | 106535679 | A | 3/2017 |
| CN | 106659858 | A | 5/2017 |
| CN | 106723372 | A | 5/2017 |
| CN | 107252138 | A | 10/2017 |
| CN | 206895827 | U | 1/2018 |
| CN | 107770883 | A | 3/2018 |
| CN | 107822205 | A | 3/2018 |
| CN | 207151935 | U | 3/2018 |
| CN | 108185534 | A | 6/2018 |
| CN | 207653582 | U | 7/2018 |
| EP | 2 460 423 | | 6/2012 |
| GB | 2533135 | A | 6/2016 |
| JP | 2008545943 | A | 12/2008 |
| WO | 2015/081554 | A1 | 6/2015 |

OTHER PUBLICATIONS

Second Chinese Office Action dated May 28, 2020 corresponding to counterpart patent application 201810723694.X.
English Abstract of CN 204317489 U.
English Abstract of CN 102264420 A.
English Abstract of CN 106659858 A.
English Abstract of CN 206895827 U.
English Abstract of CN 105707981 A.
English Abstract of CN 107770883 A.
English Abstract of CN 104770877A.
English Abstract of CN 105077598 A.
English Abstract of CN 204032371 U.
English Abstract of CN 105982360A.
English Abstract of CN 207151935 U.
English Abstract of CN 107822205 A.
English Abstract of CN 108185534 A.
ISR for International Application PCT/CN2017/088733 dated Mar. 20, 2018.
Written Opinion for International Application PCT/CN2017/088733 dated Mar. 20, 2018.
ISR for International Application PCT/CN2017/100778 dated Mar. 21, 2018.
Written Opinion for International Application PCT/CN2017/100778 dated Mar. 21, 2018.
Canadian Office Action dated Sep. 22, 2021.
Canadian Office Action dated Feb. 17, 2021 corresponding to counterpart Canadian patent application 3,048,473.
English translation of 1st Office Action corresponding to copending application CN201710457376.9 (the Chinese version has been filed).
2nd Office Action corresponding to copending application CN201710457376.9 dated Oct. 21, 2019.
1st Office Action corresponding to copending application CN201710797391.8 dated May 20, 2023.
1st Office Action corresponding to copending application CN201720710115.9 dated Nov. 29, 2017.

* cited by examiner

HEATING INHALER AND CONTROLLING METHOD THEREOF

CROSS-REFERENCE TO RELATED APPLICATION

This application claims the benefit of Chinese Patent Application No. 201810723694X, entitled "Heating Inhaler and Controlling Method Thereof", and filed on Jul. 4, 2018, the entire content of which is incorporated herein in its entirety.

TECHNICAL FIELD

The present disclosure relates to an inhaler, and particularly relates to a heating inhaler and a controlling method thereof.

BACKGROUND

With the deepening of smoking and health research, some scientific studies have shown that most of the substances in cigarettes that endanger the human body are produced by pyrolysis of tobacco during burning. To solve the problem, a group of companies, such as Philip Morris Inc., have developed electric heating smoking devices to release nicotine and other components through electrically heating of tobacco, tobacco products or tobacco product analogues, avoiding harmful substances produced by tobacco burning.

Additionally, in the field of medicine, inhalation therapy is often used for treatment, and it is often necessary to use a number of inhalers that have a heating function to treat patients by heating the medicine to release the effective substance contained in the medicine.

However, the conventional beating inhalers can only simply heat the medicine, but cannot meet the needs of different patients for different medicines, so it is very inconvenient to operate.

SUMMARY

According to various embodiments of the present disclosure, a controlling method and a heating inhaler for implementing the method are provided.

According to a method of controlling a heating inhaler, the heating inhaler includes a power source supplying power to the heating inhaler, an atomizer detachably connected to the power source, a sensing element, an indicating element, and a control circuit board. The power source, the atomizer, the sensing element, and the indicating element are electrically coupled to the control circuit board when the atomizer is assembled to the power source.

The method includes:

step S101: detecting, by the sensing element, a suction action, performing step S102 upon detecting the suction action within a first predetermined time period; otherwise, performing step S103;

step S102: controlling, by the control circuit board, the power source to supply power to the atomizer for a second predetermined time period and then stop supplying power to the atomizer, the indicating element displays a first state within the second predetermined time period until the power source stops supplying power to the atomizer, then the indicating element displays a second state; and step S103: controlling, by the control circuit board, the power source to stop supplying power to the atomizer, and displaying, by the indicating element, the second state.

In the heating inhaler for implementing the aforementioned method, the atomizer includes a housing and a heating assembly, the housing has a hollow structure to form an atomizing cavity capable of accommodating the heating assembly, and one end of the housing away from the power source is provided with a mouthpiece in communication with the atomizing cavity. The atomizer is detachably connected to the power source, and the housing of the atomizer and a casing of the power source are provided with an air inlet hole at a junction therebetween. The air inlet hole is in communication with the atomizing cavity. When an air flow flows into the housing through the air inlet hole and flows to the atomizing cavity, the sensing element senses a change of the air flow and detects a suction action, and the control circuit board adjusts an operation state of the heating inhaler according to a detection result of the sensing element.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

Embodiments of the present disclosure are described more fully hereinafter with reference to the accompanying drawings. The various embodiments of the present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art.

It will be understood that when an element is referred to as being "fixed" to another element, it can be directly fixed to the other element or intervening elements may be present. Also, when an element is referred to as being "connected" or "coupled" to another element, it can be directly connected or coupled to the other element or intervening elements may be present. As used herein, the terms "inside", "outside", "left", "right" and the like are merely for the illustrative purpose.

In one embodiment, a method of controlling a heating inhaler is provided. In order to facilitate description of the method, the structure of the heating inhaler implementing the method is exemplarily described, but is not intended to limit the method.

Figure 1:
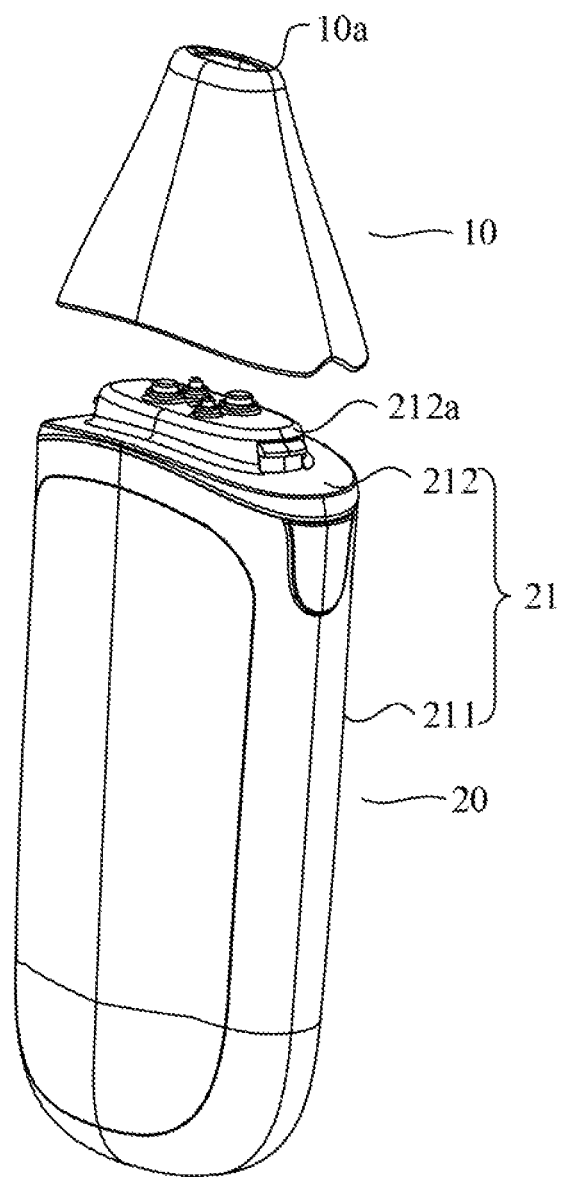
FIG. 1 is a perspective view of a heating inhaler according to an embodiment with an atomizer and a power source separated.
Figure 4:
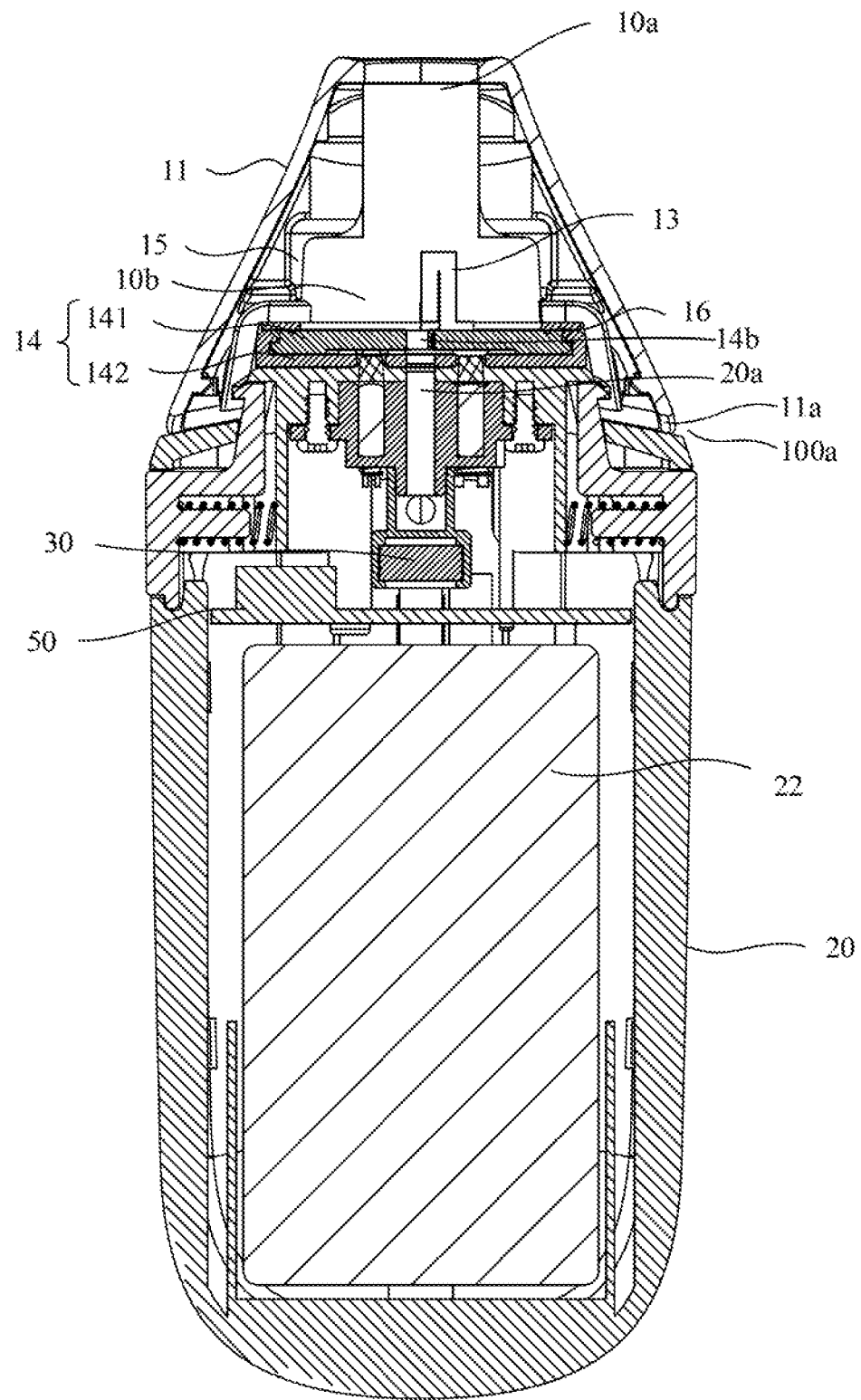
FIG. 4 is a cross-sectional view of a heating inhaler according to an embodiment.
Figure 8:
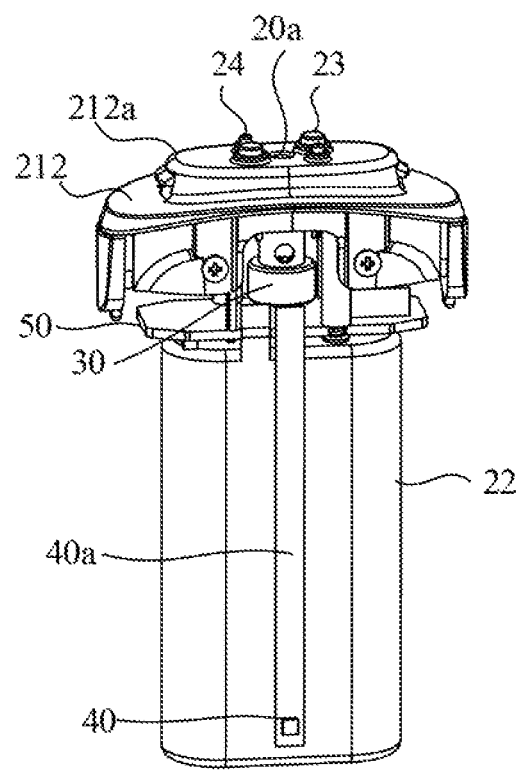
FIG. 8 is a perspective view of an internal structure of a power source of a heating inhaler according to an embodiment.

Referring to FIG. 1, FIG. 4, and FIG. 8, the heating inhaler 100 includes an atomizer 10, a power source 20, a sensing element 30, an indicating element 40, and a control circuit board 50. The atomizer 10 is detachably connected to the power source 20. The power source 20 is used to supply power to the heating inhaler 100.

It should be noted that the atomizer 10, the sensing element 30, the indicating element 40, and the control circuit board 50 are all powered by the power source 20. In other words, before the power source 20 is assembled to the heating inhaler 100 (referring to the state in FIG. 1), the atomizer 10, the sensing element 30, and the indicating element 40 of the heating inhaler 100 are in a power-off state, which means that these elements are in an off state. It should be noted that, when the power source 20 is assembled to the heating inhaler 100, the power source 20, the atomizer 10, the sensing element 30, and the indicating element 40 are electrically coupled to the control circuit board 50. Thus, the control circuit board 50 controls the functions of the power source 20 such as on, off, and on duration is realized by the control circuit board 50, thereby adjusting an operation state of the heating inhaler 100.

The method includes:

In step S101, the sensing element 30 detects a suction action.

If the sensing element 30 detects the suction action within a first predetermined time period, step S102 is performed. That is, the control circuit board 50 controls the power source 20 to supply power to the atomizer 10 for a second predetermined time period, then stop supplying power to the atomizer 10. The indicating element 40 displays a first state within the second predetermined time period until the power source 20 stops supplying power to the atomizer 10, then the indicating element 40 displays a second state.

If the sensing element 30 does not detect the suction action within the first predetermined time period, step S103 is performed. That is, the control circuit board 50 controls the power source 20 to stop supplying power to the atomizer 10, and the indicating element 40 displays the second state.

It should be noted that, the first state may be an initial state of the indicating element 40 when the atomizer 10 is electrically coupled to the power source 20, so as to indicate that the atomizer 10 completes the electrical coupling to the power source 20, and the control circuit board 50 can control the power source 20 to adjust the heating state of the atomizer 10. The indicating element 40 may be a state indicator lamp to prompt the user of the operation state of the heating inhaler 100 by the illuminating state of the state indicator lamp. For example, the first state refers to that when the state indicator lamp emits green light, the atomizer 10 is energized with the power source 20, and the corresponding suction action can be performed. Correspondingly, the second state may be a state in which the state indicator lamp is off, and the second state may also be that the state indicator lamp changes the emitting color.

Additionally, as described above, before the atomizer 10 is assembled to the power source 20, the atomizer 10, the sensing element 30, and the indicating element 40 of the heating inhaler 100 are in the power-off state, which means that these elements are in the off state. Therefore, the time at which the atomizer 10 is electrically coupled the power source 20 (hereinafter referred to as "initial time") is the start time at which the sensing element 30 is turned on by the power source 20 to detect the suction action. The initial time is also the start time of the first predetermined time period.

In the present embodiment, since the sensing element 30 can detect whether there is a suction action within the first predetermined time period, the control circuit board 50 can adjust the operation state of the heating inhaler 100 according to the detection result of the sensing element 30, improving the convenience of the operation. The first predetermined time period and the second predetermined time period may be predetermined according to the actual substance to be atomized, thereby meeting different requirements of atomization.

Hereinafter, the aforementioned method will be further described by taking the substance to be atomized as a certain medicine as an example.

For example, the medicine will fail in 15 minutes after unpacking, that is, the user have to take it within 15 minutes after placing the medicine in the atomizer 10, otherwise the medicine will lose its effectiveness. The first predetermined time period is set to 15 minutes in a predetermined manner. During this 15 minutes, the sensing element 30 senses a suction action, and if the suction action is sensed, the atomizer 10 heats the medicine to be atomized for the user to inhale. Correspondingly, if no suction action is sensed before the medicine fails (that is, within the 15 minutes), the medicine loses its effectiveness due to expiring, and the control circuit hoard 50 controls the power source 20 to stop supplying power to the atomizer 10, and the indicating element 40 displays a second state, such that the user can know that the medicine has lost its effectiveness according to the change in the state of the indicating element 40. The second state may be a state in which the state indicator lamp is off, or the second state may also be that the state indicator lamp changes the emitting color. For example, in the first state, the state indicator lamp is displayed in green. Correspondingly, in the second state, the state indicator lamp is switched from green to yellow, such that the user can know the operation state of the atomizer 10 according to the state displayed by the state indicator lamp.

In some cases, the atomizer 10 can completely atomize the medicine by heating the medicine for only a certain time period. Accordingly, the second predetermined time period is set according to the duration required for heating the medicine to completely atomize the medicine, such that it can be ensured that when the sensing element 30 detects the suction action, the atomizer 10 can completely atomize the medicine within the second predetermined time period in which the power source 20 supplies power to the atomizer 10. Also, when the atomization of the medicine is completed, that is, after the power source 20 supplies power to the atomizer 10 for the second predetermined time period, the control circuit board 50 controls the power source 20 to stop the power supply. This configuration is more advantageous when the heating time required for the complete atomization of the medicine is less than the user's inhaling time. It can avoid the waste of electric energy due to the atomizer 10 burning in empty state, improve the time of endurance of the power source 20 of the heating inhaler 100, and effectively prolong the service life of the atomizer 10 and the sensing element 30 of the heating inhaler 100.

For example, if the atomizer 10 can completely atomize the medicine by heating the medicine for two seconds, the second predetermined time period can be set to two seconds in a predetermined manner. Therefore, when the sensing element 30 detects the suction action, the control circuit board 50 controls the power source 20 to supply power to the atomizer 10 for the second predetermined time period, that is, for 2 seconds, such that the medicine is completely atomized.

In some embodiments, when the indicating element 40 is a state indicator lamp, during the process that the control circuit board 50 controls the atomizer 10 to heat and atomize the medicine, the state indicator lamp may prompt the user that the atomizer 10 is in the operation state of heating and atomizing, the medicine by gradually lightening. For example, during the first predetermined time period, the sensing element 30 detects the suction action, the green light displayed by the state indicator lamp gradually lights up to the brightest and remains. After the power source 20 supplies power to the atomizer 10 for the second predetermined time period, since the atomizer 10 has completely atomized the medicine, the control circuit board 50 controls the power source 20 to stop supplying power to the atomizer 10, and accordingly, the state indicator lamp is off.

In some embodiments, the method further includes a step S203. In step S203, the control circuit board 50 determines whether a time interval between a time at which the atomizer 10 is electrically coupled to the power source 20 and a time at which the sensing element 30 detects a suction action in a previous time is greater than a third predetermined time period. The step S101 is performed if the time interval is greater than the third predetermined time period. Otherwise, the control circuit board 50 controls the power source 20 to stop supplying power to the atomizer 10, and the indicating element 40 displays a third state. The third predetermined time period may be set according to the minimum time interval for taking the medicine. For example, if the time interval between twice of taking some medicines need to be 30 minutes, the third predetermined time period is set to 30 minutes. Therefore, the control state can be determine by the time interval from which the suction action is detected by the sensing element 30, so as to know whether taking the medicine with the heating inhaler 100 is in conformity with the administration standard of the medicine. In other words, only if the time interval is greater than the third predetermined time period, the user can inhale and take the medicine by the heating inhaler 100 again. If the time interval is not greater than the third predetermined time period (i.e., 30 minutes), the indicating element 40 can prompt the user by displaying the third state. In this way, it is effectively ensured that users are able to take the medicine according to the taking standard to ensure better efficacy while avoiding the adverse effects due to improper taking of the medicine. When the indicating element 40 is a state indicator lamp, the third state may be displaying an indicator color such as a red light, a blue light, or the like.

It should be noted that, the indicating element 40 may also include a display screen, which presents the first state, the second state, and the third state in a manner of displaying characters or patterns, which can also achieve a similar prompting effect, and will not described in detail herein.

In some embodiments, the first predetermined time period ranges from 10 minutes to 20 minutes, the second predetermined time period ranges from 1.5 seconds to 2.5 seconds, and the third predetermined time period ranges from 25 minutes to 35 minutes, so as to accommodate the need for the heating inhaler 100 to atomize the medicine for the user to inhale.

In some cases, when the power is low, the indicating element 40 can also prompt the power accordingly. When an output voltage of the power source 20 is lower than an operation voltage of the heating inhaler 100, the indicating element 40 flashes and switches between the different states. For example, if the operation voltage of the heating inhaler 100 is 3.75V, the indicating element 40 flashes and switches between the different states when the output voltage of the power source 20 is less than 3.75 V, prompting the user to charge the heating inhaler 100. If the indicating element 40 is a state indicator lamp, the state indicator lamp may flash red light as a prompt signal to prompt the user that the power source 20 has a low power.

Referring to FIG. 1, FIG. 4, and FIG. 8, the heating inhaler 100 for implementing the aforementioned method is further provided. The heating inhaler 100 includes the atomizer 10, the power source 20, the sensing element 30, the indicating element 40, and the control circuit board 50. The power source 20 is used to supply power to the heating inhaler 100. The power source 20, the atomizer 10, the sensing element 30, and the indicating element 40 are electrically coupled to the control circuit board 50.

Figure 3:
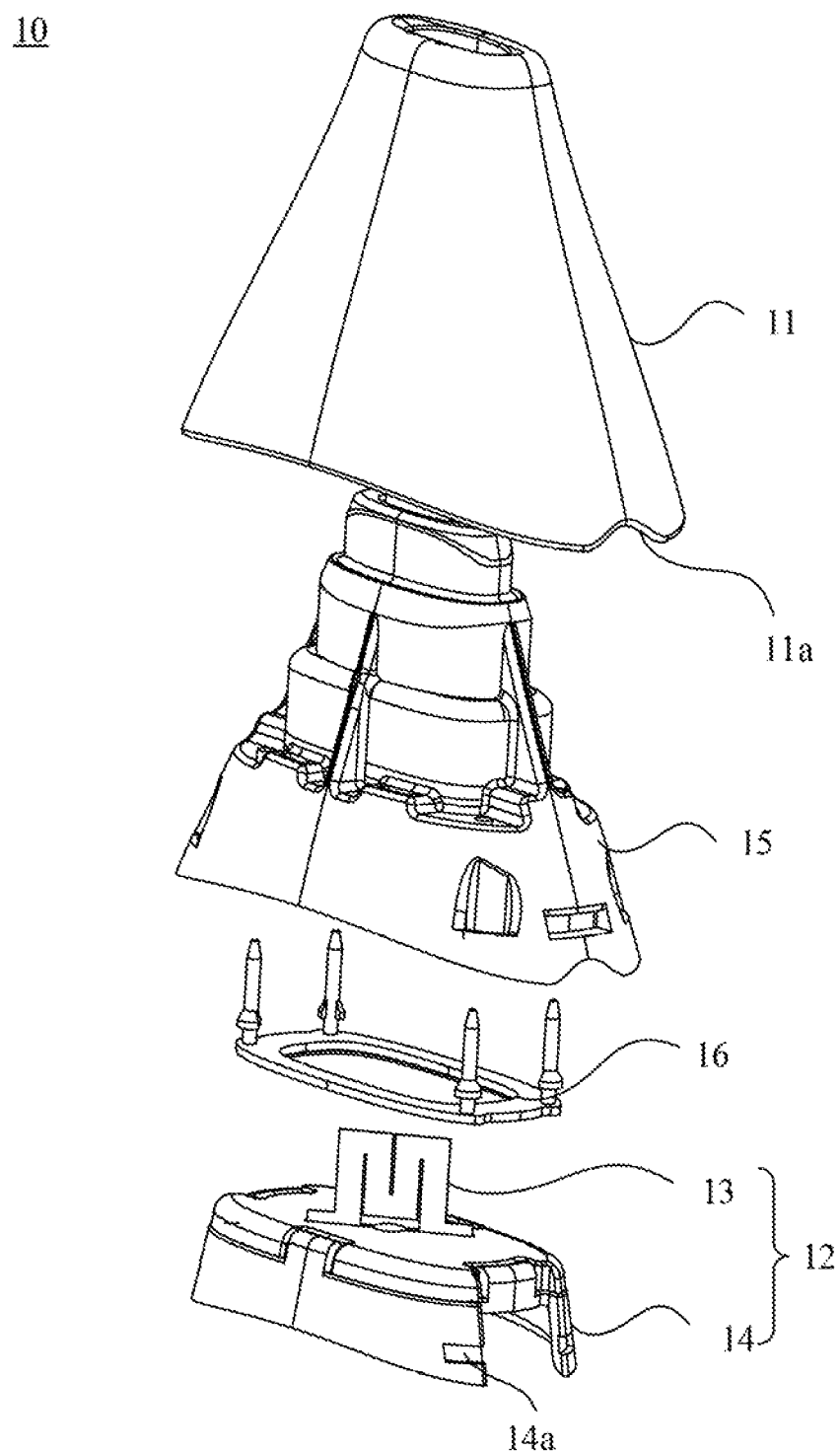
FIG. 3 is an exploded view of the atomizer of the heating inhaler of FIG. 1.
Figure 5:
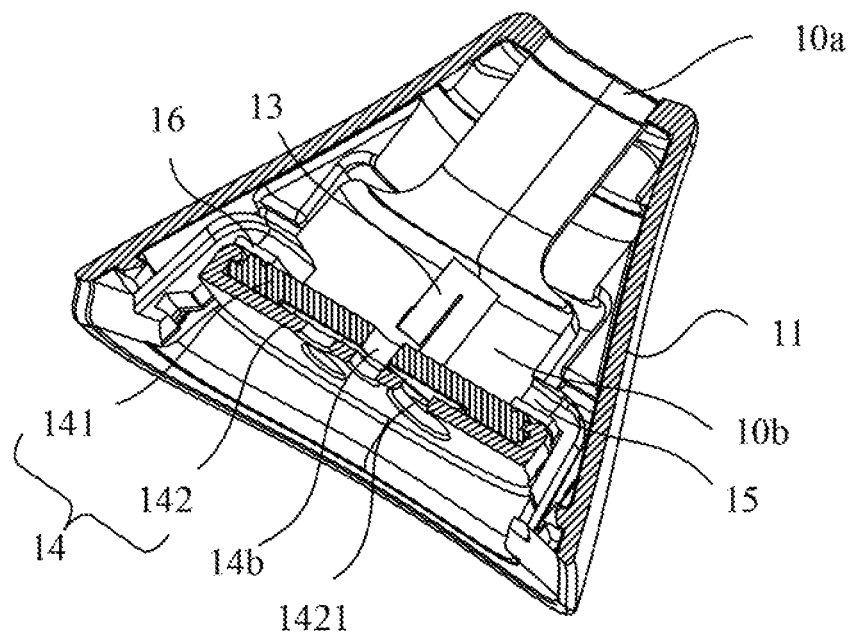
FIG. 5 is a cross-sectional view of an atomizer according to an embodiment.

Referring to FIG. 3 to FIG. 5, the atomizer 10 includes a housing 11 and a heating assembly 12. The housing 11 has a hollow structure to form an atomizing cavity 10b capable of accommodating the heating assembly 12, and one end of the housing 11 away from the power source 20 is provided with a mouthpiece 10a in communication with the atomizing cavity 10b.

Figure 2:
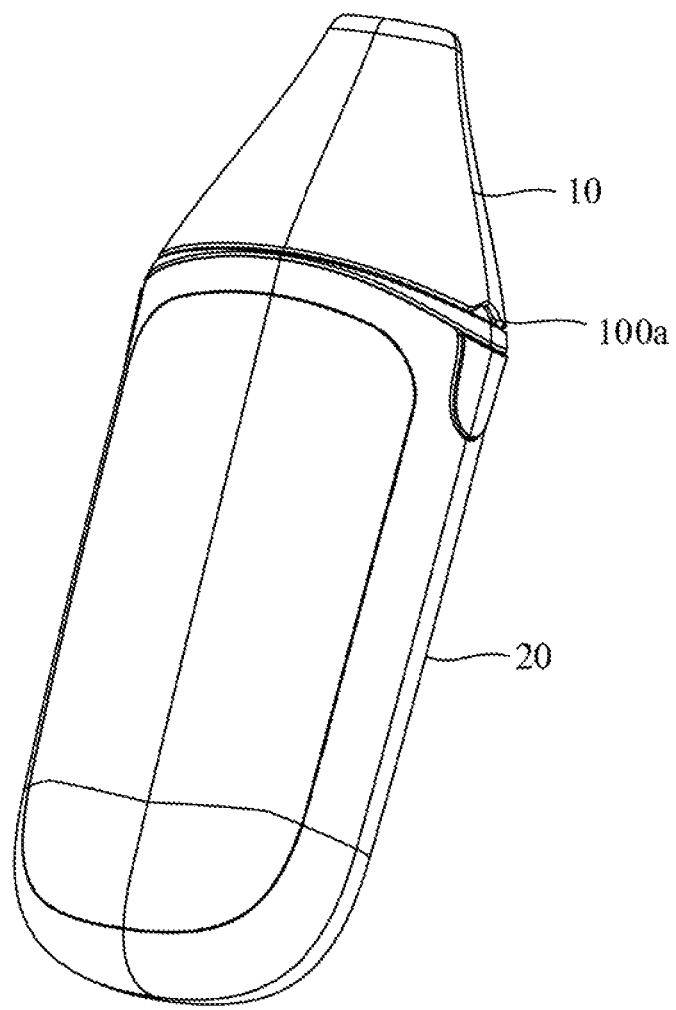
FIG. 2 is a perspective view of the heating inhaler of FIG. 1 with the atomizer and the power source assembled.

Also referring to FIG. 2, the atomizer 10 is detachably connected to the power source 20. The housing 11 of the atomizer 10 and a casing 21 of the power source 20 are provided with an air inlet hole 100a at a junction therebetween, such that external air flow can flow into the atomizer 10 through the air inlet hole 100a and take away the medicine heated and atomized by the atomizer 10 for the user to inhale.

Referring to FIGS. 3 and 4, the housing 11 and the casing 21 may cooperatively form the air inlet hole 100a when the housing 11 is assembled to the casing 21. For example, one end of the housing 11 adjacent to the power source 20 is provided with a notch 11a, such that when the housing 11 is engaged with the casing 21, the notch 11a and a side of the casing 21 adjacent to the atomizer 10 cooperatively form the air inlet hole 100a, such that the external air flow can flow into the atomizer 10.

The air inlet hole 100a is in communication with the atomizing cavity 10b, such that when the user sucks the mouthpiece 10a, the external air flow flows into the atomizing cavity 10b through the air inlet hole 100a and carries the medicine atomized by the heating assembly 12 to the mouthpiece 10a for the user to inhale.

Specifically, when the external air flow flows into the housing 11 through the air inlet hole 100a and flows to the atomizing cavity 10b, the sensing element 30 can detect the suction action by sensing the change of the air flow. The control circuit board 50 can adjust the operation state of the heating inhaler 100 according to the detection result of the sensing element 30. The position of the sensing element 30 is not particularly limited, for example, the sensing element 30 may be disposed on an air passage between the an inlet hole 100a and the atomizer 10, and the air flow generated by the suction action is detected. In addition, as shown in FIGS. 1, 4, and 8, the sensing element 30 is disposed in the casing 21 of the power source 20. The casing 21 of the power source 20 is provided with a vent hole 20a in communication with the air inlet hole 100a. Therefore, when the external air flow flows into the atomizer 10 through the air inlet hole 100a, the air flow flows through the surface of the casing 21 of the power source 20 adjacent to the atomizer 10, such that a negative pressure is generated at the vent hole 20a on the casing 21, thus the sensing element 30 can detect the suction action by sensing the change of the air flow according to the detected negative pressure value.

Figure 7:
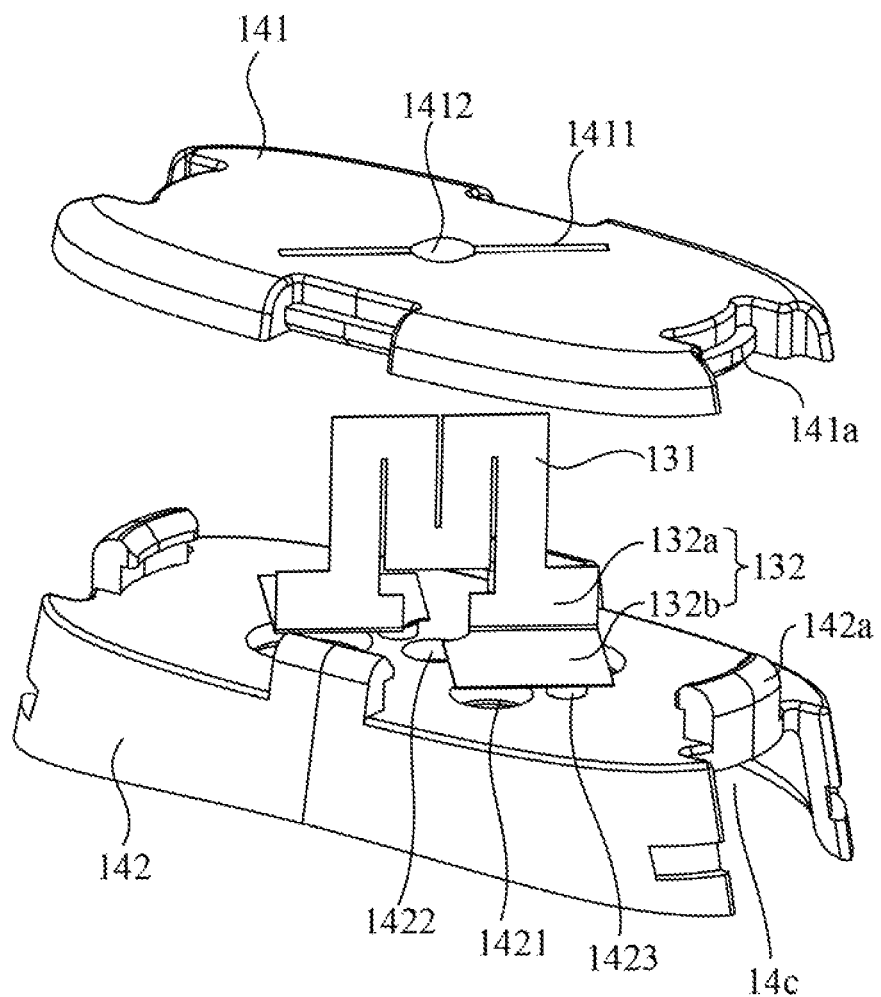
FIG. 7 is an exploded view of a heating assembly of an atomizer according to an embodiment.

Referring to FIG. 3, FIG. 5, and FIG. 7, the heating assembly 12 includes a heating sheet 13 and a fixing base 14. The fixing base 14 is detachably connected within the housing 11 of the atomizer 10, and the heating sheet 13 is detachably mounted on the fixing base 14.

It should be noted that, the detachable connection between the fixing base 14 and the housing 11 of the atomizer 10 may have various configurations. For example, a latching groove 14a is provided on an outer wall of the fixing base 14, and an inner wall of the housing 11 of the atomizer 10 is provided with a rib (not shown) corresponding to the latching groove 14a, such that the fixing base 14 connected with the heating sheet 13 is mounted in the housing 11 of the atomizer 10 by a snap fit between the rib and the latching groove 14a.

As shown in FIG. 3, a rubber member 15 is embedded in the housing 11 of the atomizer 10, and the rubber member 15 is adapted to the housing 11 of the atomizer 10. The rubber member 15 forms the atomizing cavity 10b therein, that is, the hollow portion formed in the rubber member 15 is the atomizing cavity 10b. On the one hand, the rubber member 15 is provided to facilitate the engagement with the fixing base 14, on the other hand, the rubber member 15 is provided to realize thermal insulation using a gap between the rubber member 15 and the inner wall of the housing 11, such that the heat is prevented from being transferred from the heating sheet 13 to the outer surface of the housing 11 during heating, thereby preventing the user from being scalded during inhaling the atomized medicine through the mouthpiece 10a.

As shown in FIG. 4 and FIG. 8, the fixing base 14 is provided with a through hole 14b corresponding to the vent hole 20a of the casing 21 of the power source 20. The connection portion between the fixing base 14 and the rubber member 15 is sealed by a sealing member 16. Therefore, when the air flow flows into the atomizing cavity 10b through the fixing base 14, no air leaks between the fixing base 14 and the rubber member 15, such that when the air flow entering through the air inlet hole 100a flows into the atomizing cavity 10b through the through hole 14b, a significant suction effect can he generated at the vent hole 20a on the casing 21 of the power source 20 to form a large negative pressure, such that the sensing element 30 provided in the casing 21 of the power source 20 detects the change of the negative pressure value, thereby realizing the detection of the suction action. Accordingly, the control circuit board 50 controls the operation states of the power source 20, the atomizer 10, and the indicating element 40 according to the detection result of the sensing element 30.

Figure 6:
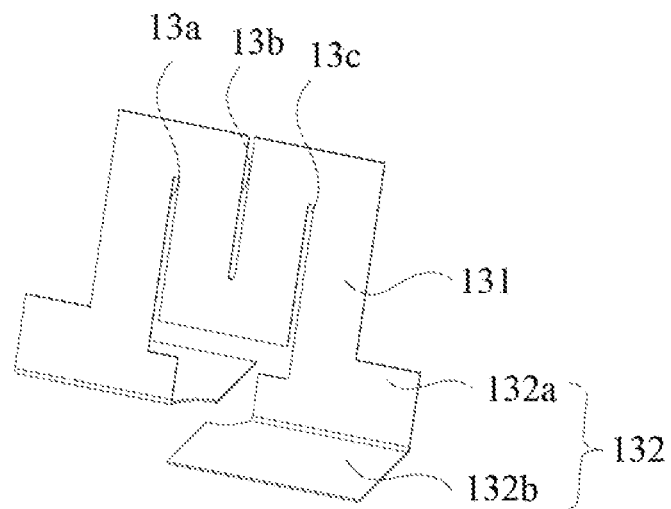
FIG. 6 is a perspective view of a heating sheet of an atomizer according to an embodiment.

Referring to FIG. 6, the heating sheet 13 includes a heating portion 131 and an electrical coupling portion 132 connected to each other. The heating portion 131 includes at least one slit structure to separate the heating portion 131 into a plurality of heating units in series. Therefore, the heating efficiency of each of the heating units can be different by adjusting the width of each of the heating units. In addition, the entire heating portion 131 can heats uniformly by adjusting the heating efficiency of each of the heating units, such that one end of the heating portion 131 connected to the electrical coupling portion 132 is prevented from losing heat faster than the other end of the heating portion 131 away from the electrical coupling portion 132 during heat conduction, resulting in nonuniform heating of the heating portion 131.

In some embodiments, the heating portion 131 includes three slit structures arranged sequentially, which are a first slit structure 13a, a second slit structure 13b, and a third slit structure 13c. The first slit 13a and the third slit 13c extend from a bottom side of the heating portion 131 to a top side thereof, respectively, and the second slit 13b extends from the top side of the heating portion 131 to the bottom side thereof, such that the heating portion 131 is separated into four heating units in series. The heating efficiency of each of the heating units can be balanced by adjusting the widths of the corresponding heating units, such that the entire heating portion 131 can uniformly heat, thereby improving the atomizing performance.

When a paste-like or gel-like medicine is atomized, by the heating inhaler 100, the medicine may be applied on one surface or both surfaces of the heating sheet 13, such that when the power source 20 supplies power to the electrical coupling portion 132 to heat the heating portion 131, the medicine on the surface of the heating sheet 13 is heated and atomized into a gas for the user to inhale. Additionally, the medicine may be prepared in a form of a film or a block, and may be attached to the heating portion 131, such that the medicine can also be well heated and atomized.

As shown in FIG. 6, in some embodiments, the electrical coupling portion 132 includes a horizontal portion 132a and a vertical portion 132b. The horizontal portion 132a is connected between the heating portion 131 and the vertical portion 132b, and is located on the same plane where the heating portion 131 located. The horizontal portion 132a is perpendicular to the vertical portion 132b, the horizontal portion 132a is parallel to an axial direction of the atomizer 10, and the vertical portion 132b is perpendicular to the axial direction of the atomizer 10.

Referring to FIG. 7, the fixing base 14 includes a cover 141 and a base 142, and the cover 141 is provided with a slot 1411. The horizontal portion 132a of the electrical coupling portion 132 extends through the slot 1411, and the vertical portion 132b is fixed between the cover 141 and the base 142, so as to fasten the heating portion 131 of the heating sheet 13. During fastening the heating sheet 13, the horizontal portion 132a of the electrical coupling portion 132 may be passed through the slot 1411 of the cover 141, and then the portion of the electrical coupling portion 132 passing through the slat 141 may be bent, thereby forming the vertical portion 132b.

It should be noted that, since the through hole 14b extends through the cover 141 and the base 142, the external air flow entered the junction between the housing 11 and the casing 21 through the air inlet hole 100a can flow into the atomizing cavity 10b through the through hole 14b. In the illustrated embodiment, the cover 141 is provided with a first through hole 1412, and the base 142 is provided with a second through hole 1422. When the cover 141 and the base 142 are assembled together, the first through hole 1412 and the second through hole 1422 are aligned to each other to cooperatively form the through hole 14b.

In some embodiments, a protrusion 1423 is provided on an upper surface of the base 142, and the protrusion 1423 is located opposite to the vertical portion 132b. Since the vertical portion 132b is fixed between the base 142 and the cover 141, the vertical portion 132b is located on the upper surface of the base 142, when the heating sheet 13 is fixed, the protrusion 1423 can press the vertical portion 132b against the cover 141, so as to prevent the vertical portion 132b from moving between the base 142 and the cover 141, and the mounting stability of the heating sheet 13 is improved.

Also referring to FIG. 7, in some embodiments, the base 142 and the cover 141 are fixed by latching connection.

Specifically, the base 142 is provided with a buckle 142a, and the cover 141 is provided with a buckle groove 141a engaged with the buckle 142a. When the cover 141 is fastened to the base 142, the vertical portion 132b is clamped between the protrusion 1423 and the cover 141.

It should be noted that, the base 142 and the cover 141 may be fixed not only by the above-mentioned latching connection, but also, by other detachable connections such as screwing.

Referring to FIGS. 1, 5, 7, 8, and 9, the power source 20 includes a battery 22 and two conductive structures. The battery 22 is mounted in the casing 21 of the power source 20, and the two conductive structures are electrically coupled to the positive and negative electrodes of the battery 22, respectively.

The casing 21 of the power source 20 includes a bottom casing 211 and a top cover 212. The bottom casing 211 has a battery cavity for receiving the battery 22. After the battery 22 is received in the bottom easing 211, the top cover 212 and the bottom casing 211 are detachably connected to each other, so as to cover an opening of the battery cavity for placing the battery 22.

In some embodiments, each of the conductive structures includes a conductive contact 23 and a spring (not shown). The conductive contact 23 is mounted on the casing 21 of the power source 20, and the conductive contact 23 is elastically abutted against the electrical coupling portion 123 under an elastic force of the spring, such that the electrical coupling portion 132 is electrically coupled to the positive and negative electrodes of the battery 22 via the conductive contact 23. Thus the conductive contact 23 abuts against the electrical coupling portion 132 of the heating sheet 13.

It should be noted that, the conductive structure is located on the top cover 212, and when the atomizer 10 is connected to the power source 20, an end of the conductive contact 23 adjacent to the atomizer 10 can abut against the electrical coupling portion 132 of the heating sheet 13. Specifically, the base 142 is provided with a hole position 1421 corresponding to the electrical coupling portion 132, and the end of the conductive contact 23 adjacent to the atomizer 10 is exposed from the surface of the top cover 212, such that when the atomizer 10 is connected to the power source 20, the end of the conductive contact 23 exposed from the top cover 212 can be in contact with the heating sheet 13 through the hole position 1421, thereby realizing the electrical coupling between the battery 22 and the heating sheet 13.

As shown in FIG. 8, a portion of the top cover 212 where the conductive contact 23 is disposed forms a raised plug portion 212a. Correspondingly, the fixing base 14 for mounting the heating sheet 13 is provided with a recessed portion 14c adapted to the plug portion 212a, such that the conductive contact 23 located on the plug portion 212a inserts into the recessed portion 14c of the fixing base 14 and abuts against the electrical coupling portion 132 of the heating sheet 13 when the plug portion 212a is plugged and engaged into the recessed portion 14c.

The vent hole 20a is located on the top cover 212, and the sensing element 30 is received in a cavity cooperatively formed by the top cover 212 and the bottom casing 211. The sensing element 30 can sense the negative pressure generated at the vent hole 20a by the air flow flowing through the surface of the top cover 212, such that when the user inhales at the mouthpiece 10a of the atomizer 10, the sensing element 30 can detect a suction action, such that the control circuit board 50 determines the operation state of the atomizer 10 according to whether the suction action is detected. For example, if the suction action is detected in the first predetermined time period, the atomizer 10 operates to heat and atomize the medicine for the user to inhale. Alternatively, if no suction action is detected in the first predetermined time period, since the medicine fails after the first predetermined time period, the control circuit board 50 controls the power source 20 to stop supplying power to the atomizer 10, so as to prevent the user from inhaling the failed medicine.

In some of the embodiments, the control circuit board 50 includes a temperature control circuit. The heating sheet 13 is made of a material having a temperature coefficient of resistance, and the temperature control circuit is electrically coupled between the heating sheet 13 and the battery 22. The temperature control circuit is used to regulate a voltage or current applied to the heating sheet 13 by the battery 22, so as to change the heating temperature of the heating sheet 13.

It should be noted that, the temperature control circuit may be connected to the heating sheet 13 by means of an electrical probe contact. As shown in FIG. 8, the plug portion 212a of the top cover 212 is correspondingly provided with an elastic probe 24 electrically coupled to the temperature control circuit. The elastic probe 24 is configured such that the elastic probe 24 can abut against the electrical coupling portion 132 of the heating sheet 13 in the atomizer 10 when the atomizer 10 is connected to the power source 20, such that the temperature control circuit can detect the current or voltage between the electrical coupling portions 132 through the elastic probe 24, and the resistance value of the heating sheet 13 can be obtained according to the measured current value or voltage value in combination with the output power of the power source 20. In addition, the temperature of the heating sheet 13 can be determined by the temperature coefficient of resistance of the heating sheet 13, thereby facilitating adjusting the temperature of the heating sheet 13. For example, when the temperature of the heating sheet 13 is higher than the predetermined temperature range, the output power of the battery 22 is reduced, thereby reducing the heating efficiency of the heating sheet 13 and returning the temperature to the predetermined temperature. When the temperature of the heating sheet 13 is lower than the predetermined temperature range, the output power of the battery 22 is increased, thereby improving the heating efficiency of the heating sheet 13 and returning the temperature to the predetermined temperature. It should be noted that, the predetermined temperature is the set temperature when the heating inhaler 100 is used, that is, the predetermined temperature can be set to a certain temperature according to different needs, or the predetermined temperature can also be set to a certain temperature range, which will not be repeated here.

Referring to FIG. 8, the bottom casing 211 is provided with a recess 2111 on an outer side wall thereof, so as to receive the indicating element 40. For example, if the indicating element 40 is a display screen, the display screen can be received in the recess 2111 and electrically coupled to the control circuit board 50. In general, the indicating element 40 can meet the requirement of the prompt function by using the state indicator lamp. The state indicator lamp can be located on a light bar 40a electrically coupled to the control circuit board 50, and the light bar 40a is received in the recess 2111.

In the illustrated embodiment, a decorative surface casing 213 is mounted on the bottom casing 211 to cover the recess 2111, such that the heating inhaler 100 can have a better overall texture.

Figure 9:
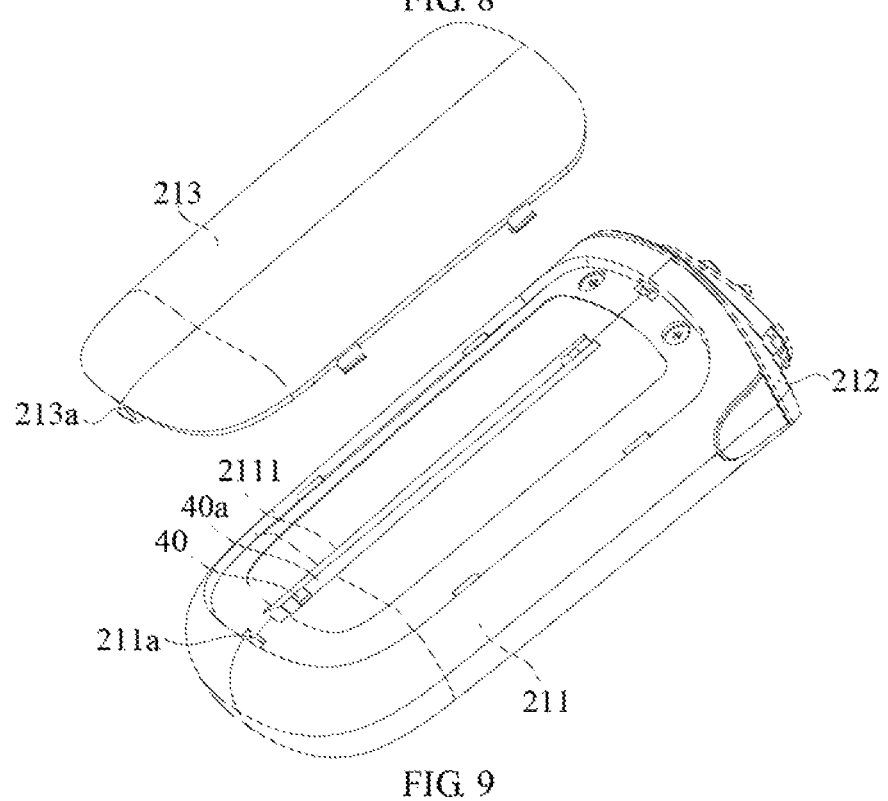
FIG. 9 is a perspective view of a casing of a power source of a heating inhaler according to an embodiment.

Referring to FIG. 9, the decorative surface casing 213 may be connected to the side wall of the bottom casing 211 by a snap fit. For example, a plurality of clips 213a are provided on one side of the decorative surface casing 213 facing the bottom casing 211, and correspondingly, the side wall of the bottom casing 211 is provided with a plurality of clip grooves 211a corresponding to the clips 213a. Therefore, when the clip 213a is engaged with the clip groove 211a, the decorative surface casing 213 is stably connected to the bottom casing 211, thereby shielding the indicating element 40, so as to obtain a better appearance.

It should be noted that, the decorative surface casing 213 does not affect the indicating effect of the indicating element 40. For example, when the indicating element 40 is a state indicator lamp, the decorative surface casing 213 has a better light transmittance at a position corresponding to the state indicator lamp, such that the state indicator lamp can transmit light of different colors to indicate the corresponding state. Of course, the decorative surface casing 213 may be provided with holes for exposing the outer surface of the indicating element 40, which will not be described in detail here.

The technical features of the embodiments described above can be arbitrarily combined. In order to make the description succinct, there is no describing of all possible combinations of the various technical features in the foregoing embodiments. It should be noted that there is no contradiction in the combination of these technical features which should be considered as the scope of the description.

Although the present disclosure is illustrated and described herein with reference to specific embodiments, the present disclosure is not intended to be limited to the details shown. It is to be noted that, various modifications may be made in the details within the scope and range of equivalents of the claims and without departing from the present disclosure. Therefore, the protection scope of the present disclosure shall be subject to the protection scope of the claims.

What is claimed is:

1. A method of controlling a heating inhaler, wherein the heating inhaler comprises a power source configured to supply power to the heating inhaler, an atomizer detachably connected to the power source, a sensing element, an indicating element, and a control circuit board; the power source, the atomizer, the sensing element, and the indicating element are electrically coupled to the control circuit board when the atomizer is assembled to the power source; the method comprises: step S101: detecting, by the sensing element, a suction action, performing step S102 upon detecting the suction action within a first predetermined time period; otherwise, performing step S103;

step S102: controlling, by the control circuit board, the power source to supply power to the atomizer for a second predetermined time period, and then to stop supplying power to the atomizer, wherein the indicating element displays a first state within the second predetermined time period until the power source stops supplying power to the atomizer, then the indicating element displays a second state; and step S103: controlling, by the control circuit board, the power source to stop supplying power to the atomizer, and displaying, by the indicating element, the second state; further comprising step S203: determining, by the control circuit board, a time interval between a time at which the atomizer is electrically coupled to the power source and the time at which the sensing element detects a suction acution in a previous time is greater than a third predetermined time period, performing the step S101 upon determining that the time interval is greater than the third predetermined time period; otherwise, controlling, by the control circuit board, the power source to stop supplying a power to the atomizer, and the indicating element displaying a third state;

wherein the first predetermined time period ranges from 10 minutes to 20 minutes, the second predtermined time period ranges from 1.5 seconds to 2.5 seconds, and the third predetermined time period ranges from 25 minutes to 35 minutes.

2. The method according to claim 1, wherein the indicating element comprises a state indicator lamp, the first state, the second state, and the third state indicate three operation states of the state indicator lamp, respectively.

3. The method according to claim 2, wherein the second state indicates that the state indicator lamp is in an off state.

4. The method according to claim 2, wherein the second state indicates that the state indicator lamp changes an emitting color thereof.

5. The method according to claim 1, wherein the indicating element flashes and switches between different states when an output voltage of the power source is less than 3.75 V.

6. The method according to claim 1, wherein the indicating element comprises a display screen.

* * * * *